United States Patent [19]

Rabbani

[11] Patent Number: 4,889,798

[45] Date of Patent: Dec. 26, 1989

[54] HETEROLOGOUS SYSTEM FOR THE DETECTION OF CHEMICALLY LABELED DNA AND OTHER BIOLOGICAL MATERIALS PROVIDING A RECEPTOR OR TARGET MOIETY THEREON

[75] Inventor: Elazar Rabbani, New York, N.Y.

[73] Assignee: Enzo Biochem, Inc., New York, N.Y.

[21] Appl. No.: 15,563

[22] Filed: Feb. 13, 1987

Related U.S. Application Data

[63] Continuation of Ser. No. 578,732, Feb. 9, 1984, abandoned.

[51] Int. Cl.$^4$ .................. C12Q 1/68; C07H 21/00; C12N 9/96; G01N 33/53
[52] U.S. Cl. .......................... 435/6; 435/810; 435/188; 435/803; 435/7; 935/78; 436/808; 436/824; 436/827; 536/27; 530/367; 548/303
[58] Field of Search .................. 435/6, 7, 188, 810, 435/803; 436/501, 518, 808, 824, 827; 935/78; 536/27; 530/367, 395, 396; 548/303

[56] References Cited

U.S. PATENT DOCUMENTS

| | | |
|---|---|---|
| 4,298,685 | 11/1981 | Parikh et al. |
| 4,334,017 | 6/1982 | Plotkin et al. |
| 4,395,486 | 7/1983 | Wilson et al. ................. 436/504 X |
| 4,455,380 | 6/1984 | Adachi . |
| 4,478,914 | 10/1984 | Giese . |
| 4,550,075 | 10/1985 | Becquet et al. ................ 435/188 X |
| 4,581,333 | 4/1986 | Kourilsky et al. ............. 435/188 X |
| 4,687,732 | 8/1987 | Ward et al. ...................... 435/6 |

OTHER PUBLICATIONS

Leary, J. J. et al., *Proc. Natl. Acad. Sci. USA*, vol. 80, Jul., 1983, pp. 4045–4049.
Langer, P. R. et al., *Proc. Natl. Acad. Sci. USA*, vol. 78, No. 11, Nov. 1981, pp. 6633–6637.

*Primary Examiner*—Johnnie R. Brown
*Assistant Examiner*—Jeremy M. Jay
*Attorney, Agent, or Firm*—Charles J. Herron; Serle I. Mosoff

[57] ABSTRACT

In accordance with the practices of this invention, there is provided a heterologous detection system and components useful in conjunction therewith and kits for carrying out the heterologous detection system. The heterologous detection system employs a heterologous entity and a signalling entity. The heterologous entity contains two free complex forming sites that form different complexes, i.e., two kinds of complexes can be formed. The first free complex forming site is utilized to recognize the labeled probe and the second free complex forming site is utilized to recognize the signalling entity, with each complex formed being different. The signalling entity contains a free complex forming site that can recognize the second free complex forming site of the heterologous entity and a signalling portion that is capable of generating a signal. An example of a heterologous detection system that can be utilized to detect biotinylated probe is a system that contains a heterologous entity comprising avidin and a lectin and a signalling entity comprising a glycosylated enzyme. The avidin can recognize the biotin of the probe and the lectin can recognize the glycosyl group of the enzyme. The enzyme is capable of generating a signal when treated with a suitable reagent. Such a heterologous detection system provides both a quick and highly sensitive technique for detecting a biotinylated probe.

24 Claims, No Drawings

HETEROLOGOUS SYSTEM FOR THE DETECTION OF CHEMICALLY LABELED DNA AND OTHER BIOLOGICAL MATERIALS PROVIDING A RECEPTOR OR TARGET MOIETY THEREON

This is a continuation of application Ser. No. 578,732, filed February 9, 1984, entitled HETEROLOGOUS SYSTEM FOR THE DETECTION OF CHEMICALLY LABELED DNA AND OTHER BIOLOGICAL MATERIALS PROVIDING A RECEPTOR OR TARGET MOIETY THEREON.

BACKGROUND OF THE INVENTION

The use of labeled molecules as probes for the detection of other molecules, such as DNA or other materials, is as important activity from a commercial, diagnostic and scientific point of view. Historically, the labels utilized for such purposes have been radioactively labeled with isotopes of hydrogen ($^3$H), phosphorous ($^{32}$P), carbon ($^{14}$C), or iodine ($^{125}$I). Such radioactive compounds provide useful probes that permit the user to detect, monitor, localize or isolate the labeled molecule of interest. To date, radioactive materials have provided the most sensitive, and in many cases, the only means to perform many important experimental or analytical tests. There are, however, serious limitations and drawbacks associated with the use of radioactive compounds. First, since personnel who handle radioactive material can be exposed to potentially hazardous levels of radiation, elaborate safety precautions must be maintained during the preparation, utilization, and disposal of the radioisotopes. Second, radioactive labeled molecules are extremely expensive to purchase and use, in large part due to the cost of equipment and manpower necessary to provide the appropriate safeguards, producer/user health monitoring services and waste disposal programs. Third, radioactive materials are often very unstable and have a limited shelf life, which further increases usage costs. This instability results from radiolytic decomposition due to the destructive effects associated with the decay of the radioisotope itself and from the fact that many isotopes have half lives of only a few days.

Recently it has been discovered that chemically labeled probes can be utilized in place of radioactively labeled probes. For example, probes consisting of nucleotides labeled with biotin that are capable of being incorporated into double stranded DNA have been prepared. The single stranded DNA labeled with biotin is capable of detecting its target, a complementary single stranded DNA, by hybridizing with such complementary single stranded DNA. The presence of the biotinylated nucleotide in the hybridized double stranded DNA is detected by utilizing the strong affinity of avidin for biotin which results in the formation of a stable biotin/avidin complex. The binding constant for the biotin/avidin complex is about $10^{-16}$. Also attached to the avidin, which has four binding sites for biotin, is a biotinylated enzyme, such as biotinylated horseradish peroxidase, which is capable of generating a signal when treated with a suitable reagent. Streptavidin can be used as a substitute for avidin. The utilization of streptavidin or avidin for the detection of biotinylated nucleotides or biotinylated DNA is disclosed in European Patent Application Publication No. 0,063,879, published March 11, 1983. This European Patent Application Publication is derived from U.S. application Ser. No. 225,223 filed April 17, 1981. The disclosures of the above referred European Patent Application Publication and the U.S. Application are herein incorporated and made part of this disclosure.

It has also been proposed to label nucleotides with glycosyl groups, such as maltose, lactose, mannose, maltose triose and mannose triose. Such labeled nucleotide can be recognized with a lectin, such as Concanavalin A. Lectins possess an affinity for glycosyl groups, albeit the affinity of a lectin for a glycosyl group is not nearly as strong as the affinity of avidin for biotin. The binding constant is about $10^{-4}$. Thus, a glycosyl group/lectin complex is formed. Attached to a lectin, which has four binding sites for a glycosyl group, is a glycosylated enzyme, such as alkaline phosphatase or acid phosphatase. The glycosylated enzyme is capable of creating a signal when treated with a suitable reagent. This detection system is disclosed in co-pending co-assigned U.S. patent application Ser. No. 391,440 filed June 23, 1982 now abandoned. The disclosures of this U.S. Patent Application are herein incorporated and made part of this disclosure.

Each of the above detection systems is a homologous detection system. A homologous detection system contains only one kind of complex forming site, i.e., biotin/avidin or glycosyl group/lectin. The same affinity is utilized to (1) recognize the label of the probe and (2) connect a moiety that is capable of generating a signal to the detection system. Thus, for example, the affinity between avidin and biotin is utilized to recognize the biotinylated probe and to connect a biotinylated enzyme to avidin, the enzyme being capable of generating a signal when treated with a suitable reagent.

SUMMARY OF THE INVENTION

In accordance with the practices of this invention, there is provided a heterologous detection system and components useful in conjunction therewith and kits for carrying out the heterologous detection system. The heterologous detection system employs a heterologous entity and a signalling entity. The heterologous entity contains two free complex forming sites that form different complexes, i.e., two kinds of complexes can be formed. The first free complex forming site is utilized to recognize the labeled probe and the second free complex forming site is utilized to recognize the signalling entity, with each complex formed being different. The signalling entity contains a free complex forming site that can recognize the second free complex forming site of the heterologous entity and a signalling portion that is capable of generating a signal. An example of a heterologous detection system that can be utilized to detect a biotinylated probe is a system that contains a heterologous entity comprising avidin and a lectin and a signalling entity comprising a glycosylated enzyme. The avidin can recognize the biotin of the probe and the lectin can recognize the glycosyl group of the enzyme. The enzyme is capable of generating a signal when treated with a suitable reagent. Such a heterologus detection system provides both a quick and highly sensitive technique for detecting a biotinylated probe.

The process of the practices of this invention comprises a method of detecting the presence of a labeled probe which comprises:
(A) providing:
 (i) a heterologous entity wherein said heterologous entity comprises:

(a) at least one first free complex forming site, and
(b) at least one second free complex forming site, wherein said first free complex forming site is capable of recognizing the label of said probe and said first free complex forming site and said second free complex forming site form different complexes; and
(ii) a signalling entity wherein said signalling entity comprises:
(a) at least one third free complex forming site, and
(b) a signal generating portion, wherein said third free complex forming site is capable of recognizing said second free complex forming site of said heterologous entity;
(B) forming a complex comprising:
said heterologous entity complexed through said first free complex forming site to said label of said probe and said heterologous entity complexed through said second free complex forming site to said third free complex forming site of said signalling entity; and
(C) creating a signal by means of said signal generating portion of said complex.

DETAILED DESCRIPTION OF THE INVENTION

By way of background information, avidin is a glycoprotein having a molecular weight of about 68,000. The binding of avidin to biotin is essentially irreversible and comparable to a covalent bond. Streptavidin, a material closely related to avidin, can be, and is preferred to be, substituted in place of avidin, particularly in the connection with the detection of labeled DNA. This is due to the fact that avidin has a tendency to non-specifically interact with DNA. However, unlike avidin, streptavidin is not naturally glycosylated.

Lectins are proteins or glycoproteins that recognize a specific sequence of sugar residues. Lectins were originally isolated from plants where they are found in large quantities in many seeds. Lectins, however, subsequently have been found in all types of organisms.

Numerous lectins are commercially available. Some commerically available lectins and the specific sugar residues they recognize are set forth in the following table:

TABLE

| Lectins | Sugar Specificity |
|---|---|
| Concanavalin A | Alpha-glucose and alpha-D-mannose |
| Soybean lectin | D-galactose and N—acetyl-D-galactosamine |
| Wheatgerm lectin | N—acetyl glucosamine |
| Lotus seed lectin | fucose |
| Potato lectin | N—acetyl glucosamine |
| Dilichos biflorus agglutinin | N—acetyl galactose-aminyl |
| Lentil lectin | Alpha-D-mannose and alpha-D-glucose |

This invention relates to a heterologous detection system and components useful in conjunction therewith and kits for carrying out the heterologous detection system. The heterologous detection system is utilized to detect the presence of a labeled probe. The system employs a heterologous entity and a signalling entity.

The heterologous entity contains two free complex forming sites that are capable of forming two different complexes. "Free" means that the complex forming site is not bound to the molecule which it recognizes. The first free complex forming site is utilized to recognize the label of the probe. Recognition means the non-covalent binding between complementary portions of two molecules to form a complex. The second free complex forming site is utilized to recognize the free complex forming site of the signalling entity. Each of the two complex forming sites can be either a ligand or a receptor. A ligand and receptor are entities wherein each has a complex forming site that recognizes the complex forming site of the other wherein the ligand is generally the smaller entity. However, it is preferred that the first free complex forming site be a receptor. Otherwise, the probe would be labeled with a receptor which, due to its large size as compared to its ligand, would probably inhibit the probe from detecting its target.

It is essential that each of the two complex forming sites of the heterologous entity be able to form two different complexes. As discussed hereinbelow, the formation of two different complexes provides a quicker and/or more sensitive technique for detecting a labeled probe than by utilizing a homologous detection system based on either the first free complex forming site or the second free complex forming site.

The signalling entity contains a free complex forming site that is capable of recognizing the second free complex forming site of the heterologous entity and a signal generating portion. The free complex forming site contained in the signalling entity is utilized to recognize the second free complex forming site of the heterologous entity. For example, if the second free complex forming site of the heterologous entity is a lectin, then the free complex forming site of the signalling entity must be the corresonding glycosyl group.

The signal generating portion of the signalling entity encompasses virtually any of the signal generating systems used in the prior art and any system to be developed in the future. It comprises a moiety which generates a signal itself, e.g., a dye, or radioactive molecule or a moiety which upon further reaction or manipulation will give rise to a signal, e.g., an enzyme linked system.

Suitable enzymes that can be utilized as the signal generating portion of the signalling entity are essentially any enzyme that is capable of generating a signal when treated with a suitable reagent. Preferred enzymes are horseradish peroxidase, alkaline-phosphatase, glucose oxidase, peroxidase, acid phosphatase and B-galactosidase, all of which are naturally glycosylated. Such enzymes are preferred because they are very stable, yet highly reactive.

The heterologous detection system within the practices of the invention provides a quicker and/or more sensitive technique for detecting a labeled probe than a homologous detection system based on either the first free complex forming site or the second free complex forming site of the heterologous entity. Without being bound by theory, it is believed that a heterologous detection system provides such benefits because a heterologous detection system can utilize only that portion of a homologous detection system that is very effective and there are more free complex forming sites available to form the desired complex. This can be explained as follows:

For example, consider a heterologous detection system that is based on the affinity between avidin and biotin and the affinity between a lectin and a glycosyl group. The corresponding homologous detection systems would be based on the affinity between avidin and biotin or the affinity between a lectin and a glycosyl group. As discussed hereinbefore, in the biotin/avidin homologous detection system avidin recognizes the biotinylated probe. A signal is capable of being generated by having a biotinylated enzyme attached to at least one of the complex forming sites of avidin. Due to the extremely strong affinity between avidin and biotin, avidin recognizes the biotinylated probe very quickly and forms an extremely stable complex. However, this system is not very sensitive due to the fact that the enzyme must be biotinylated to be recognized by avidin. This pretreatment of the enzyme destroys some of its activity. On the other hand, a lectin of a glycosyl group/lectin homologous detection system forms a less stable complex with a glycosylated probe than avidin does with a biotinylated probe because the glycosyl group/lectin affinity is not as strong as the biotin/avidin affinity. But, a glycosyl group/lectin homologous detection system has the potential of being very sensitive because the glycosylated enzyme can be recognized by the lectin. Thus, the enzyme need not be pretreated which can destroy some of its activity. The heterologous detection system within the practices of this invention combines the quick reactivity of the biotin/avidin homologous detection system with the high sensitivity of the glycosyl group/lectin homologous detection system.

Further, all of the first free complex forming sites of the heterologous entity can be utilized to recognize the label of the probe and all of the second free complex forming sites of the heterologous entity can be utilized to recognize the signalling entity. At least one of the complex forming sites of avidin or lectin in a homologous detection system must be free in order for the avidin or lectin to recognize the signal generating entity. Thus, the avidin or lectin in such system plays two roles, it must recognize the label of the probe and it must recognize the signal entity. There is no such competition for the complex forming sites in the heterologous detection systems of the practices of the invention. All of the first free complex forming sites of the heterologous entity can be utilized to recognize the label of the probe and all of the second free complex forming sites of the heterologous entity can be utilized to recognize the signalling entity. It is believed that this too contributes to the high speed and/or sensitivity of the heterologous detection system within the practices of the invention.

In the heterologous detection systems in accordance with this invention, a preferred embodiment thereof resides in the use of the combination involving the affinity between biotin and avidin or biotin and streptavidin and the affinity between a glycosyl group and a lectin (and any analogs or derivatives of these). Such two affinities can, through many combinations and permutations, form numerous different heterologous entities and signalling entities, all of which are within the practices of this invention. The choice of which to form is based upon whether the probe is labeled with biotin or a glycosyl group and the ease of preparation of the system.

By way of example, with a biotinylated probe, such as biotinylated DNA, the heterologous entity can comprise streptavidin and a lectin, such as Concanavalin A. This entity can be formed by conjugation by methods analogous to those disclosed in M. J. O'Sullivan and V. Marks, *Methods in Enzymology*, 73, 147–166 (1981), published by Academic Press. This entity can also be formed by glycosylating streptavidin and then forming a complex with a lectin or by forming a streptavidin biotinylated enzyme complex, wherein the enzyme is glycosylated and thus, forming a complex with a lectin. Such heterologous entity contains two free complex forming sites that form different complexes, those on the streptavidin and those on the lectin.

The signalling entity for such heterologous entity can be a glycosylated enzyme. The glycosyl group can recognize the lectin. The resulting complex that is formed is a biotinylated DNA/streptavidin/lectin/enzyme complex. A signal can be created by contacting the enzyme with a suitable reagent.

This heterologous entity, i.e., streptavidin and a lectin, can also be utilized to detect a probe labeled with a glycosyl group, e.g., glycosylated DNA. In this instance the signalling entity can be a biotinylated enzyme. A preferred technique for the preparation of biotinylated enzymes is disclosed in co-pending, co-assigned U.S. patent application Ser. No. 486,924, filed April 20, 1983 now abandoned. This patent application, the disclosures of which are herein incorporated and made a part of this disclosure, discloses a technique for the biotinylation of enzymes, such as alkaline phosphatase. This technique can further be utilized to complex the biotinylated enzyme to the streptavidin. (It should be noted that this technique can also be used to connect a non-glycosylated enzyme to a lectin.) Thus, the lectin can then recognize the glycosyl group of the glycosylated DNA and streptavidin can recognize the biotin of the biotinylated enzyme. The resulting complex is a glycosylated DNA/lectin/streptavidin/biotinylated enzyme complex. A signal can be created by contacting the complex with a suitable reagent.

Another heterologous entity that can be utilized based upon the same two affinities is an entity comprising avidin and a lectin. Such entity can be made by forming a complex between avidin and a lectin. This is because avidin, unlike streptavidin, is naturally glycosylated. Depending on what the probe is labeled with, a signalling entity can be a biotinylated enzyme or an enzyme containing a glycosyl group.

Yet another heterologous entity based upon the same two affinities is a biotinylated lectin. This entity can be formed by covalently linking biotin to a lectin. Biotinylated lectins are commercially available from Vector Laboratories, Inc., Burlingame, California. This entity can recognize a probe labeled with a glycosyl group. A signalling entity for this heterologous entity comprises avidin or streptavidin and a biotinylated enzyme.

Still another heterologous entity based upon the same two affinities is avidin, which is naturally glycosylated, or streptavidin that is glycosylated. These entities can recognize a biotinylated probe. A signalling entity for these heterologous entities can comprise a lectin with a signalling portion attached thereon. Such signalling portion can be a glycosylated enzyme that is capable of generating a signal when treated with a suitable reagent.

Yet another heterologous entity based upon the same two affinities is avidin or streptavidin that is biotinylated with a glycosylated enzyme. This entity can recognize a biotinylated probe. The signalling entity for such heterologous entity can comprise a lectin which contains as the signal generating portion a glycosylated enzyme.

Finally, another heterologous entity based upon the same two affinities is a lectin that is complexed with a glycosylated enzyme that is biotinylated. This entity can recognize a probe labeled with a glycosyl group. The signalling entity for this heterologous entity can comprise an avidin or streptavidin which is complexed to a biotinylated enzyme.

The techniques for the employment of a labeled probe in the identification of DNA are disclosed in co-pending co-assigned patent application Ser. No. 461,469 now abandoned, filed January 27, 1983, the disclosures of which are herein incorporated and made part of this disclosure. The techniques disclosed therein are applicable to the heterologous detection systems in accordance with this invention. There are described in this patent application techniques for the analysis of genetic material, such as DNA and RNA, wherein the genetic material is to be analyzed with a probe, such as a labeled probe having a nucleotide sequence complementary to the target genetic material. Such techniques comprise denaturing and fixing the target genetic material to a matrix. The target genetic material is then contacted with the denatured labeled probe so as to permit hybridization. After hybridization, those probes that did not hybridize to the target genetic material are separated from those probes that did hybridize to the target genetic material. Any separation means can be utilized with a preferred means being washing the target genetic material with a neutral solution to remove those probes that did not hybridize to the target genetic material. After the probe has been hybridized with the DNA or RNA to be identified, the detection system is added which can recognize the label of the probe and is capable of creating a detectable signal. The target genetic material is then typically separated once again, preferably by washing with a neutral solution, to remove those detection system moieties that did not recognize the label of the probe. It is stated that spectrophotometric or colorimetric techniques can be utilized to detect the hybridized probe. Co-pending, co-assigned patent application Ser. No. 574,632 filed Jan. 26, 1984 the disclosure of which are herein incorporated and made part of this disclosure, discloses a similar method for the detection of a labeled probe. However, this method utilizes a detection system that results in the formation of an insoluble color precipitate or product.

Similarly, the heterologous detection system can be added after the probe has been hybridized with the DNA to be identified. It can be utilized to create a detectable signal via spectrophotometric or colorimetric techniques or by the formation of an insoluble color precipitate or product. The heterologous entity and the signalling entity can be added to the sample either sequentially or as a preformed complex. When the heterologous entity and signalling entity are added sequentially, the sample, e.g., target genetic material should be separated from the heterologous entities that did not complex with the sample and the signalling entities that did not complex with the heterologous entities complexed with the sample. Such separation can be carried out by washing the sample with a neutral solution. Therefore, it is preferred to add the heterologous entity and signalling as a preformed complex; this requires only one separation step. The heterologous detection system of this invention is especially useful in such well known analytical techniques, such as Southern blots analysis, Northern blots analysis, Western blots analysis, colony hybridization, plaque lifts and other analytical techniques for the identification of genetic material such as DNA and RNA.

It is preferred in the practices of this invention that the probe be a polynucleotide, and preferably DNA or RNA. However, the probe can be any substance which can recognize any target which is the probes corresponding molecule. Nonlimiting examples of other probes and their recognizable targets include an antigen probe to be recognized by its corresponding monoclonal or polyclonal antibody, an antibody probe to be recognized by its corresponding antigen, a lectin probe to be recognized by its corresponding sugar, a sugar probe to be recognized by its corresponding lectin, a hormone probe to be recognized by its receptor, a receptor probe to be recognized by its hormone, an enzyme probe to be recognized by its inhibitor, a cofactor probe to be recognized by its apoenzyme and an apoenzyme probe to be recognized by its cofactor.

It is believed that the heterologous entity and the signalling entity can be based on affinities other than the affinity between biotin and avidin or biotin and streptavidin and the affinity between a lectin and glycosyl group. It is believed that essentially any affinity can be utilized in the practices of this invention. For example, the heterologous entity can be avidin or streptavidin which can recognize a biotinylated probe which is utilized with a signalling entity that can be a monoclonal or polyclonal antibody to avidin or streptavidin that has an enzyme attached thereto. Thus, the affinity between an antibody and its antigen can be utilized herein. It should be noted that in such system that the heterologous entity is just one entity, but such entity contains two free complex forming sites that are capable of forming different complexes. Other affinities that can be utilized as components of heterologous and signalling entities are the affinities based on an enzyme and its inhibitor, a hormone and its receptor and an apoenzyme and its cofactor.

It should also be noted that the signalling entity need not have the signalling portion attached thereto prior to the addition of the signalling entity to the system. For example, a heterologous entity that is avidin can further comprise a biotinylated enzyme. A signalling entity that can be added to such system can be an antibody to avidin. When such antibody is added to the system, since an antibody has two complex forming sites, it can complex with an avidin that is in fact complexed with the label of the probe and with avidin which did not complex with the label of the probe. Thus, the resulting signalling entity is an antibody complexed with an avidin which comprises a biotinylated enzyme which was not formed until after the antibody was added to the system. This results in a more sensitive detection system than a detection system which utilizes only avidin with a biotinylated enzyme. Also, it should be noted that such antibody can be precomplexed with such heterologous entity. This too provides a very sensitive detection system.

The present invention lends itself readily to the preparation of kits comprising one or more elements necessary to perform the detection of the labeled probe. A kit may comprise a carrier being compartmentalized to receive in close confinement therein one or more container means or series of container means such as test tubes, vials, flasks, bottles, syringes, or the like. A first container means can contain a labeled probe. A second container means can contain the heterologous entity. A third container means can contain the signalling entity. It is preferred that the heterologous entity and the signalling entity are precomplexed, one container means can contain both entities. Also, a kit can be prepared which contains the components necessary to label and detect a polynucleotide probe. Such kit can contain a first container means which can contain a chemically labelled nucleotide. The second container means can contain the heterologous entity. The third container means can contain the signalling entity. The fourth container means can contain enzyme means for terminally labeling a single stranded polynucleotide probe with the chemically labeled nucleotide or for the incorporation of the chemically labeled nucleotide, such as by nick translation, to produce the chemically labeled polynucleotide probe. Since it is preferred that the heterologous entity and the signalling entity be precomplexed, one container means can contain both entities. Also, each of the above kits can further contain the elements necessary to create a signal, such as a chromogen.

Each of the above kits can further contain a substrate or maxtrix which is utilized to fix the probe thereto. For example, the matrix can be nitrocellulose paper or nylon membrane or a glass slide. The following examples are illustrative of the practices of this invention:

EXAMPLE I

DETECTION OF GLYCOSYLATED DNA

Single stranded T4 DNA was fixed to a nitrocellulose filter according to standard protocols. Ten spots on the filter were made comprising the following concentrations of T4 DNA; 500 pcg, 250 pcg, 125 pcg, 31.25 pcg, 15.626 pcg, 7.8 pcg, 3.9 pcg and 0 pcg. This filter was blocked by immersion in phosphate buffered solution containing 2% bovine serum albumin (BSA) and 0.1% Triton X-100 and 1 X SSC and incubations at 50° C. for about 12 hours. Detection of the T4 DNA was accomplished by the addition of a solution comprising biotinylated concanavalin A and buffer wherein the buffer comprised 5 mM Tris (pH 7), 1 mM $CaCl_2$, 1 mM $MnCl_2$ and a 100 mM NaCl. The concentration of the biotinylated concanavalin A in such solution was 100 ug per ml. After 60 minutes incubation at 37° C. excess biotinylated concanavalin A was washed off the filter as follows: 3 times, 20 minutes each in a buffer comprising 10 mM alfa-D-glucose, 5 mM Tris (pH 7), 1 mM $CaCl_2$, 1 mM $MnCl_2$ and a 100 mM NaCl.

Streptavidin complexed with biotinylated horseradish peroxidase and a solution comprising 1% BSA and 1 X phosphate buffered solution was added to the blot. The concentration of the streptavidin complexed with the biotinylated horseradish peroxidase was a 1/250 dilution. After 60 minutes incubation at 37° C., the excess complex was washed off the filter as follows: 3 times, 5 times each in a high salt buffer (0.5 M NaCl/10 mM phosphate buffer pH 6.5/0.1% BSA/0.05% Tween 20) and then twice, 5 minutes each in a low salt buffer (2 X SSC/0.1% BSA/0.05% Tween 20).

The horseradish peroxidase is now bound to the T4 DNA. This enzyme was then localized by the addition of DAB (diamino benzidine). 5 mg of DAB was dissolved in 10 ml 10 mM Tris pH 7.5. 200 ul of 1% cobalt chloride was added to the DAB solution, mixed, and left on ice for ten minutes in the dark. Just prior to use, 70 ul of 30% $H_2O_2$ were added to the DAB/cobalt solution. This substrate was pipetted onto the surface of the blot. Color appeared in about 10 second to about 10 minutes depending on the amount of T4 DNA on the filter. Levels of T4 DNA were detected down to the 15.625 spot.

EXAMPLE II

Detection of Cytochrome C

Polyclonal antiserum to streptavidin was raised in mice according to standard protocols. The presence of antibody to streptavidin was confirmed in a standard ELISA wherein a 1:1,000 dilution of antiserum gave an O.D. of 0.4 at 405 nm with 55 ng of streptavidin.

Various amounts of biotinylated cytochrome C were dotted directly onto two nitrocellulose filters and then air dried. The filters were blocked for 1 hour at 37° C. with a phosphate buffered solution comprising 1% bovine serum albumin (BSA). The filters were then washed 3 times with 0.01M TRIS-HCl buffer (pH 8) containing 0.3M NaCl (buffer A).

0.5 units per ml of biotinylated alkaline phosphatase complexed with streptavidin (ratio streptavidin/enzyme= 2 ug of streptavidin per unit) in buffer A was prepared containing either 1:1,000 dilution of normal mouse serum or 1:1,000 dilution of antiserum to streptavidin. Each preparation applied to one of the filters for 30 minutes at room temperature. The filters were washed 3 times with buffer A. Color was developed overnight with BCIP-NBT in buffer A. It was observed that with normal mouse serum biotin can be detected to amounts of 0.64 f moles of biotin and with antiserum to streptavidin 0.13 f moles of biotin can be detected.

As will be apparent to those skilled in the art in the light of the foregoing disclosure, many substitutions, alternations and modifications are possible in the practices of this invention without departing from the spirit or scope thereof.

What is claimed is:

1. A composition for detecting the presence or absence of an analyte in a sample, which composition comprises:

a biotinylated polynucleotide specifically bindable with said analyte; a heterologous entity comprising streptavidin and a lectin; and a signaling entity which comprises a third free complex forming site which is specifically bindable with said lectin and, attached thereto, a signal generating portion capable of forming a signal associated with detection of said analyte.

2. A composition for detecting the presence or absence of an analyte in a sample, which composition comprises:

a biotinylated polynucleotide specifically bindable with said analyte;

a heterologous entity comprising avidin and a lectin; and a signaling entity which comprises a third free complex forming site which is specifically bindable with said lectin and, attached thereto, a signal generating portion capable of forming a signal associated with detection of said analyte.

3. A composition for detecting the presence or absence of an analyte in a sample, which composition comprises:

a biotinylated polynucleotide specifically bindable with said analyte;

a heterologous entity comprising a lectin that is complexed with a glycosylated enzyme that is biotinylated; or streptavidin; and a signaling entity which comprises a third free complex forming site which is specifically bindable with said glycosylated enzyme and, attached thereto, a signal generating portion capable of forming a signal associated with detection of said analyte.

4. The composition of claims 1, 2 or 3 wherein said lectin is selected from the group consisting of Concanavalin A, soybean lectin, wheatgerm lectin, lotus seed lectin, potato lectin, dilichos biflorus agglutinin and lentil lectin.

5. The composition of claim 4 wherein said lectin is Concanavalin A.

6. A composition for detecting the presence or absence of an analyte in a sample, which composition comprises:
 a biotinylated polynucleotide specifically bindable with said analyte:
 a heterologous entity comprising avidin or streptavidin complexed with a biotinylated enzyme that is glycosylated; and
 a signaling entity which comprises a third free complex forming site which is specifically bindable with said glycosylated enzyme and, attached thereto, a signal generating portion capable of forming a signal associated with detection of said analyte.

7. A composition for detecting the presence or absence of an analyte in a sample, which composition comprises:
 a biotinylated polynucleotide specifically bindable with said analyte;
 a heterologous entity comprising streptavidin and a glycosyl group; and
 a signaling entity which comprises a third free complex forming site which is specifically bindable with said glycosyl group and, attached thereto, a signal generating portion capable of forming a signal associated with detection of said analyte.

8. A composition for detecting the presence or absence of an analyte in a sample, which composition comprises:
 a glycosylated polynucleotide specifically bindable with said analyte; a heterologous entity comprising avidin and a lectin; and
 a signaling entity which comprises a third free complex forming site which is specifically bindable with said avidin and, attached thereto, a signal generating portion capable of forming a signal associated with detection of said analyte.

9. A composition for detecting the presence or absence of an analyte in a sample, which composition comprises:
 a glycosylated polynucleotide specifically bindable with said analyte; a heterologous entity comprising streptavidin and a lectin; and
 a signaling entity which comprises a third free complex forming site which is specifically bindable with said streptavidin and, attached thereto, a signal generating portion capable of forming a signal associated with detection of said analyte.

10. A composition for detecting the presence or absence of an analyte in a sample, which composition comprises:
 a glycosylated polynucleotide specifically bindable with said analyte;
 a heterologous entity comprising biotin and a lectin; and a signaling entity which comprises a third free complex forming site which is specifically bindable with said biotin and, attached thereto, a signal generating portion capable of forming a signal associated with detection of said analyte.

11. The composition of claims 8, 9, or 10 wherein said lectin is selected from the group consisting of Concanavalin A, soybean lectin, wheatgerm lectin, lotus seed lectin, potato lectin, dilicho biflorus agglutinin and lentil lectin.

12. The composition of claim 11 wherein said lectin is Concanavalin A.

13. A kit useful for detecting the presence or absence of an analyte in a sample, which kit comprises, in packaged combination, the following:
 (a) a first container having therein a labeled probe which comprises a biotinylated polynucleotide;
 (b) a second container having therein a heterologous entity which comprises streptavidin and a lectin;
 (c) a third container having therein a signalling entity which comprises a third free complex forming site which is specifically bindable with said lectin and, attached thereto, a signal generating portion capable of forming a signal associated with detection of said analyte.

14. A kit useful for detecting the presence or absence of an analyte in a sample, which kit comprises, in packaged combination, the following:
 (a) a first container having therein a labeled probe which comprises a biotinylated polynucleotide;
 (b) a second container having therein a heterologous entity which comprises avidin and a lectin;
 (c) a third container having therein a signalling entity which comprises a third free complex forming site which is specifically bindable with said lectin and, attached thereto, a signal generating portion capable of forming a signal associated with detection of said analyte.

15. A kit useful for detecting the presence or absence of an analyte in a sample, which kit comprises, in packaged combination, the following:
 (a) a first container having therein a labeled probe which comprises a biotinylated polynucleotide;
 (b) a second container having therein a heterologous entity which comprises a lectin that is complexed with a glycosylated enzyme that is biotinylated;
 a third container having therein a signalling entity which comprises a third free complex forming site which is specifically bindable with said lectin and, attached thereto, a signal generating portion capable of forming a signal associated with detection of said analyte.

16. The kit of claims 13, 14 or 15 wherein said lectin is selected from the group consisting of Concanavalin A, soybean lectin, wheatgerm lectin, lotus seed lectin, potato lectin, dilichos biflorus agglutinin and lentil lectin.

17. The kit of claim 16 wherein said lectin is Concanavalin A.

18. A kit useful for detecting the presence or absence of an analyte in a sample, which kit comprises, in packaged combination, the following:
 (a) a first container having therein a labeled probe which comprises a biotinylated polynucleotide;
 (b) a second container having therein a heterologous entity which comprises streptavidin and a glycosyl group;

(c) a third container having therein a signalling entity which comprises a third free complex forming site which is specifically bindable with said glycosyl group and, attached thereto, a signal generating portion capable of forming a signal associated with detection of said analyte.

19. A kit useful for detecting the presence or absence of an analyte in a sample, which kit comprises, in packaged combination, the following:
   (a) a first container having therein a labeled probe which comprises a biotinylated polynucleotide;
   (b) a second container having therein a heterologous entity which comprises avidin or streptavidin complexed with a biotinylated enzyme that is glycosylated;
   (c) a third container having therein a signalling entity which comprises a third free complex forming site which is specifically bindable with said biotinylated enzyme that is glycosylated and, attached thereto, a signal generating portion capable of forming a signal associated with detection of said analyte.

20. A kit useful for detecting the presence or absence of an analyte in a sample, which kit comprises, in packaged combination, the following:
   (a) a first container having therein a labeled probe which comprises a glycosylated polynucleotide;
   (b) a second container having therein a heterologous entity which comprises avidin and a lectin;
   (c) a third container having therein a signalling entity which comprises a third free complex forming site which is specifically bindable with said avidin and, attached thereto, a signal generating portion capable of forming a signal associated with detection of said analyte.

21. A kit useful for detecting the presence or absence of an analyte in a sample, which kit comprises, in packaged combination, the following:
   (a) a first container having therein a labeled probe which comprises a glycosylated polynucleotide;
   (b) a second container having therein a heterologous entity which comprises streptavidin and a lectin;
   (c) a third container having therein a signalling entity which comprises a third free complex forming site which is specifically bindable with said streptavidin and, attached thereto, a signal generating portion capable of forming a signal associated with detection of said analyte.

22. A kit useful for detecting the presence or absence of an analyte in a sample, which kit comprises, in packaged combination, the following:
   (a) a first container having therein a labeled probe which comprises a glycosylated polynucleotide;
   (b) a second container having therein a heterologous entity which comprises biotin and a lectin;
   (c) a third container having therein a signalling entity which comprises a third free complex forming site which is specifically bindable with said biotin and, attached thereto, a signal generating portion capable of forming a signal associated with detection of said analyte.

23. The kit of claims 20, 21 or 22 wherein said lectin is selected from the group consisting Concanavalin A, soybean lectin, wheatgerm lectin, lotus seed lectin, potato lectin, dilichos bilforus agglutinin and lentil lectin.

24. The kit of claim 23 wherein said lectin is Concanavalin A.

* * * * *